United States Patent
Grodzins

[19]
[11] Patent Number: 5,910,973
[45] Date of Patent: Jun. 8, 1999

[54] RAPID X-RAY INSPECTION SYSTEM

[75] Inventor: Lee Grodzins, Lexington, Mass.

[73] Assignee: American Science and Engineering, Inc., Billerica, Mass.

[21] Appl. No.: 08/898,165

[22] Filed: Jul. 22, 1997

Related U.S. Application Data

[XX .
[60] Provisional application No. 60/022,044, Jul. 22, 1996.

[51] Int. Cl.$^6$ .................................................. G01V 5/00
[52] U.S. Cl. ................................. 378/57; 378/53; 378/54
[58] Field of Search .............................. 378/57, 51, 53, 378/54, 56, 62, 146

[56] References Cited

U.S. PATENT DOCUMENTS

| | | | |
|---|---|---|---|
| 4,366,382 | 12/1982 | Kotowski | 378/57 |
| 5,091,924 | 2/1992 | Bermbach et al. | 378/57 |
| 5,247,561 | 9/1993 | Kotowski | 378/87 |

FOREIGN PATENT DOCUMENTS

| | | |
|---|---|---|
| Wo 86/03683 | 7/1986 | WIPO . |
| WO 93/21546 | 10/1993 | WIPO . |

OTHER PUBLICATIONS

Ashford, C.B., et al.: "High–Z Liquid Scintillators Containing Tin", Nuclear Instruments & Methods In Physics Research, Section A: Accelerators, Spectrometers, Detectors and Associated Equipment, vol. 243, No. 1, 1 Feb. 1986, Amsterdam NL, pp. 131–136, XP002045349.

*Primary Examiner*—David P. Porta
*Attorney, Agent, or Firm*—Bromberg & Sunstein LLP

[57] ABSTRACT

An inspection system for automatically detecting the presence of a concealed item within an enclosure. A beam of penetrating radiation is incident on the enclosure and detected by a detector disposed on the side of the enclosure opposite to the incident beam. By scanning the relative orientation of the enclosure with respect to the beam, the penetrating radiation transmitted through the enclosure is mapped, compared with known properties of the enclosure, and the presence of material concealed within the enclosure is determined.

16 Claims, 1 Drawing Sheet

RAPID X-RAY INSPECTION SYSTEM

The present application claims priority from U.S. provisional application No. 60/022,044, filed Jul. 22, 1996, which is herein incorporated by reference.

TECHNICAL FIELD

The present invention relates to X-ray inspection systems, and, in particular, to X-ray inspection systems employing automatic object detection.

BACKGROUND OF THE INVENTION

It is desirable to determine the presence of objects, such as contraband, weapons, or explosives, that have been concealed in an enclosure, such as a shipping container, without requiring the subjective determination of a trained operator. The determination should be capable of being made while the container is in motion. In case a detection is made, a visual image should be available for verification.

SUMMARY OF THE INVENTION

In accordance with one aspect of the invention, in one of its embodiments, there is provided an inspection system for inspecting an enclosure. The inspection system has a source of penetrating radiation and a collimator for forming the penetrating radiation into a beam which is scanned with respect to the enclosure. A detector, disposed so as to intercept the component of the beam traversing the enclosure, is provided for producing flux position distribution information. The inspection system has a signal-processing means for transforming the flux position distribution information to absorption distribution information referred to the spatial frame of reference of the enclosure and a controller for determining the presence of concealed material within the enclosure based on the absorption distribution information.

In further embodiments, the source of penetrating radiation may be an x-ray source, and, particularly, an x-ray tube, and the beam may have a specified cross section such as that of a fan beam. The scanner arrangement may include a conveyor for transporting the enclosure through the beam.

In accordance with other embodiments of the invention, the detector may have a liquid scintillator having heavy metal doping including tin doping. The detector may have an array of photodetectors. The inspection system may have a computer memory for storing absorption matrices of standard enclosures and a visual display for displaying an image based on the absorption distribution matrix. In a further embodiment, a shutter may be provided for temporally gating the penetrating radiation. The inspection system may have an autocorrelator for detecting repeat patterns and significant changes of absorption of penetrating radiation as the component of the beam traverses the enclosure.

In an embodiment of a further aspect of the invention, a method is provided for detecting the presence of concealed material within an enclosure which includes the steps of illuminating the enclosure with penetrating radiation propagating substantially along a beam having an orientation with respect to the enclosure, varying the orientation of the beam with respect to the enclosure such that a component of the beam transverses the enclosure, mapping an areal distribution of penetrating radiation transmitted through the enclosure, processing the areal distribution of penetrating radiation transmitted through the enclosure to obtain an absorption distribution matrix, and determining the presence of concealed material within the enclosure. In a further embodiment of the invention, a method is provided which has the further step of comparing the absorption distribution matrix with stored absorption distribution matrices.

In accordance with yet a further aspect of the present invention, there is provided a method for detecting the presence of concealed material within an enclosure, having the steps of illuminating the enclosure with penetrating radiation propagating substantially along a beam having an orientation with respect to the enclosure; varying the orientation of the beam with respect to the enclosure such that a component of the beam traverses the enclosure; mapping an areal distribution of penetrating radiation transmitted through the enclosure; autocorrelating the areal distribution of penetrating radiation transmitted through the enclosure; and determining the presence of concealed material within the enclosure.

BRIEF DESCRIPTION OF THE DRAWING

The foregoing features of the invention will be more readily understood by reference to the following detailed description taken with the accompanying drawing which provides a schematic representation of the preferred embodiment of the invention.

DETAILED DESCRIPTION OF PREFERRED EMBODIMENTS

Figure 1:
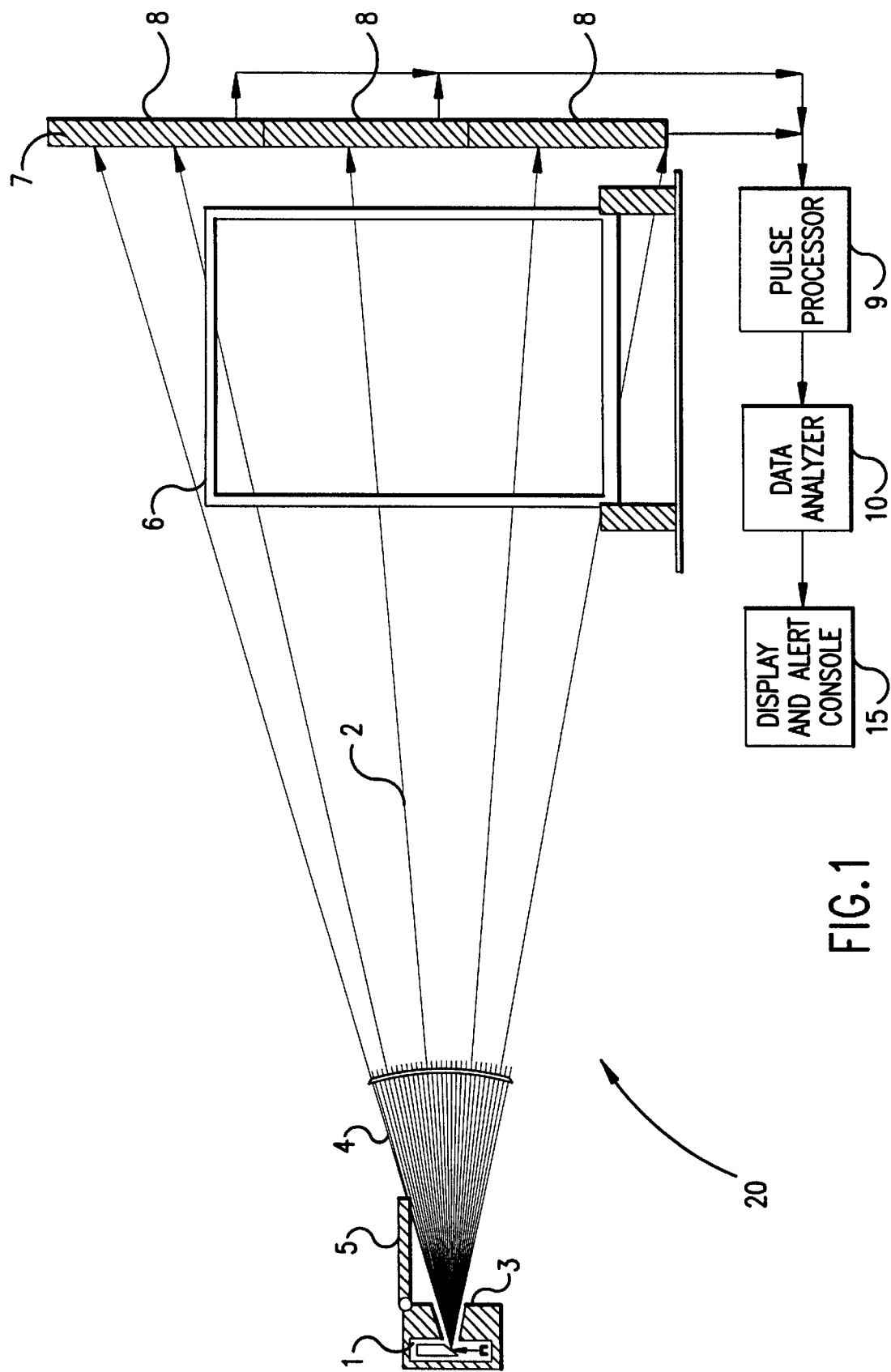

The figure shows a plan view of the elements of a rapid x-ray inspection system, designated generally by numeral 20. A source 1 emits penetrating radiation 2 through a collimator slit 3 that forms a beam 4 of predetermined cross section such as a fan beam, for example. Other structures employed in the formation of the beam into a beam of predetermined cross section are within the scope of the invention as herein described and of the appended claims. Beam 4 of penetrating radiation, may be, for example, a beam of x-rays such as a polychromatic x-ray beam. Source 1 of penetrating radiation may be an x-ray tube, for example. Beam 4 will be referred to in the present description, without limitation, as an x-ray beam, and further as a fan beam, again, without limitation. A shutter 5 controls the periods of time during which fan beam 4 is allowed to pass through a container 6, which is moving, with respect to beam 4, in a direction out of the paper. Container 6 may be self-propelled through beam 4 or may be pulled by a mechanized tractor, or by a conveyor of any sort. It is to be recognized that, equivalently, beam 4 may move with respect to container 6 in a direction into the paper. Fan beam 4, after passing through container 6, is detected by an arrangement 7 that determines a flux distribution as a function of position by measuring the intensity of the x-rays as a function of the position along detectors 8. An array of three individual detectors 8 each about 4 feet long is shown by way of example. The output signals from the detectors 8 are sent through a pulse processor 9, a data analyzer 10 and a display and alert console 15.

Inspection system 20 can be rapidly deployed in any location to inspect moving vehicles of any size to determine if their cargo container contains objects larger or heavier than a predetermined minimum. In a preferred embodiment, inspection system 20 uses a fixed fan beam 4 of x-rays to penetrate target container 6 which is moved through fan beam 4 so that every volume of container 6 is swept by x-ray beam 4. Source 1 of x-rays may be a low-power x-ray tube whose parameters are quite flexible; a highly portable x-ray tube of low power and x-ray flux may be used. In a preferred embodiment, inspection system 20 can be operated by battery or a small gasoline powered generator, and the x-ray shielding requirements, and hence the weight, are modest. As discussed in greater detail below, an x-ray tube with a terminal potential of 160 keV and an electron beam current of 125 microamps (beam power of 20 watts) is sufficient to make a rapid inspection of empty containers. An x-ray tube with these parameters may be no larger than a typical dental x-ray machine.

The geometry shown in the figure is shown solely by way of example, however the arrangement is quite flexible and in some applications it may be more advantageous to place the x-ray source and the detectors in vertical or slanted arrangements. In a preferred embodiment the x-rays are detected by long, vertical position sensitive detectors 8 made of one or more tin-doped liquid scintillators with photomultiplier tubes at appropriate positions to detect the light emitted when an x-ray interacts in the scintillator. The figure shows, as an example, three such detectors, each about 4 feet long with cross sectional dimensions of 2"×2". The use of liquid scintillators as position sensitive detectors is well known. The liquid scintillators are doped, as known to persons skilled in the art of x-ray detection, using tin or other heavy metal. The state of-the-art of this method, using photomultipliers at each end of each scintillator and standard time-of-flight techniques, results in position resolution of 1 cm. In many applications for inspection system 20, a position resolution of 5 cm is adequate, which is easily achieved with low cost components. The use of extremely fast liquid scintillators results in a simple, economical system well matched to the relatively low flux from the x-ray tube.

The signals from the photomultipliers are processed by time-of-flight coincidence techniques to determine the origin of each x-ray to within 5 cm along each 4 foot length of detector 8, typically counting at counting rates of the order of $10^7$/s.

Fan beam 4 of x-rays, 2 inches in depth passes through a cross section of the container as shown in FIG. 1. The detectors 8 produce an array of intensity values that measure the absorption of the x-rays through container 6 as a function of the height that the x-rays pass through the container. With a position resolution of 2", each 4 foot detector produces 24 intensity values. The full 12 feet of detector produces 72 intensity values for each 2" of travel of the container through the x-ray beam. The intensity, I, of x-rays passing through a container and an object, in each 2"×2" pixel of the detector is given by:

$$I=I_o \exp[-(\mu_c t_c + \mu_o t_o)] \quad (1)$$

where Io is the intensity without the container, the μ values are the mass absorption coefficients for the container walls and the object respectively, and $t_c$ and $t_o$ are the respective areal densities of the container walls and the object.

The logarithms of the ratios of these intensity values to that of the intensity values without the container are direct measures of the total attenuation of the x-rays through the container. These results are stored as an array of numbers in a computer. As the container moves through the fan beam, the computer stores successive linear arrays of numbers.

An empty container will result in a characteristic matrix of absorption values determined by the absorptions by the walls and strengthening members of trailer truck, box container, freight car, etc.

Two of the ways the invention may be used are now described. First, reference absorption matrices of standard containers can be stored in the computer memory so that the matrix of absorption values obtained during an inspection can be directly compared to quickly determine whether the container is empty. That is, since one knows the $\mu_c t_c$ values for the container, Equation 1 can be solved immediately to give the attenuation of the object.

$$\mu_o t_o = \log(I_o/I) - \mu_c t_c \quad (2)$$

Second, when the container's empty absorption matrix is not known, the identification of unexpected objects will done by a rapid correlation algorithm that finds changes in absorption values that identify unexpected objects in the supposed empty container. The absorption of the walls of the container are expected to be uniform, apart from strengthening members, so that sudden changes in the intensities, Equation 1, can be automatically detected. Strengthening members in the walls, as well as corrugated walls, produce repetitive patterns of absorption values that can be recognized by the computer algorithms. It is shown below that changes of 30% in the intensity, which correspond to relatively small objects, are easily determined. Thus, for example, a 2 inch thick package of drugs, weighing less than a pound, taped on the wall of a trailer truck, can be detected with great confidence, even when the truck is moving through the x-ray beam at 30 miles per hour.

To obtain an undistorted image of the attenuation of the x-rays through the container requires that the speed of the container with respect to the x-ray fan beam be known. In the example given here, knowledge of the speed of the container through the fan beam to an accuracy of about 5% is adequate. It should be noted, however, that neither the speed nor the rate of change of the speed need be known at all for automatic inspection for objects in empty containers. The computer algorithm for automatic inspection is based on changes in intensities over travel distances of a few inches or less. Such rapid changes cannot be caused by changes in vehicle speed since, as a simple calculation given below shows, there are practical limits to acceleration and deceleration of large vehicles.

Some of the advantages which may be obtained using the invention as described herein include:

1. The inspection system makes its decisions automatically without the need for visual aids or human judgment.

2. The inspection system automatically locates the position of the suspect object in the cargo vessel without knowledge of the speed of the vessel through the beam of penetrating radiation.

3. The inspection system automatically locates the position of the suspect object in the cargo vessel and displays information about its size and weight.

4. The inspection system is highly portable; all of the elements can be handled by a single person and can be transported in a small van, perhaps even in the trunk of a car.

5. The inspection system uses fewer than a few hundred watts of power that can be supplied by batteries, a portable generator, or from an automotive engine generator.

6. The x-rays are produced by a standard x-ray generator whose power can be turned off and on by electronic means. The generator can be taken out of the shielding which can be of modular design for easy mobility.

7. A further advantage of using the x-ray generator with electronic control is that with proper interlocks, no shutter of the beam-forming collimator is needed. The x-rays can be turned on in a fraction of a second so that the x-rays only interact with cargo and never with people in the driving cab.

8. The x-ray fluxes are very low. If a person were hidden in the cargo container he would receive an exposure of less than 100 microRoentgen of radiation; less than 5% of a standard chest x-ray.

9. The inspection system can see objects weighing but a few pounds in large containers moving at 30 mph through the system. If the Inspection system is only required to find objects weighing at least 100 pounds than the inspections can be carried out at any highway speed.

10. The inspection system can accommodate small and very large vehicles or freight cars.

To illustrate system performance, and only for purposes of example, the following typical parameters may be considered: the container is assumed to be 60 foot long by 8 feet high, with walls of ⅛" steel, moving through the x-ray beam at 44 feet/sec (30 mph), and the distance from the x-ray source to the 12 foot high detector is 30 feet, with the fan beam of x-rays projecting the 8 foot high trailer to the full 12' height of the detector. Based on the foregoing typical parameters, the average number of counts per pixel when the x-rays pass through the walls of an empty truck moving at 30 mph is ~200.

Detection sensitivity to an object in the container:

To illustrate the sensitivity of the system's performance, consider the change in count rates when a 300 gram package of drugs, 2 cm thick by 10 cm square, is taped to the side of the trailer. The counts in each pixel of drugs traversed by the x-rays will drop to an average 140 counts/pixel; a 4σ change from the 200 counts/pixel with the drug packet absent. Changes in count rates of 30% are statistically expected in several random pixels that make up the full image of the trailer, but it is highly improbable that 4 contiguous pixels will have such low counts.

The count rate in each detector pixel depends on the amount of material interposed between the x-ray source and the detector and is independent of the speed of the vehicle through the x-ray beam. In the example above, the count rate of $40 \times 10^3$/s/pixel when no object is present, changes to $25 \times 10^3$/s/pixel when the drug packet is present. The change lasts for 11 millisecs when the vehicle speed is 30 mph; 33 millisecs at a vehicle speed of 10 mph; and 5.5 ms at a speed of 60 mph. Any of these changes can be automatically and reliably detected by circuitry set to find changes in the average count rate in each pixel.

It will be appreciated that the example of a packet of drugs weighing less than 1 pound is an extreme one, used here to show the sensitivity of the invention. In practice, it is expected that the system will key on some minimum count rate change in a minimum number of contiguous pixels. The logarithm of the integrated change in the intensity levels of contiguous pixels is a good measure of the mass of the object that has produced the intensity changes. Thus, the operator can set the threshold for automatic detection on a minimum mass that results in a high probability of detecting contraband and a low false alarm rate from the casual innocuous clutter found in most "empty" containers.

The automated feature does not require a knowledge of the speed of the vehicle; that is, there will be no false alarms due to changes in the speed of the vehicle during inspection since even the most dramatic changes of speed will not alter the counts per pixel significantly. For example, an acceleration or deceleration of 20% of the acceleration of gravity leads to a change in the counts per pixel of only 0.2%, which is undetectable.

If an undistorted image of the intensity values is needed, the speed of the vehicle must be known so as to establish a length scale along the velocity axis. A measurement of the speed to an accuracy of a few percent is readily and rapidly accomplished using standard radar techniques, for example, or using any other speed measurement technique.

Cargo containers such as trailer vans are made in a wide variety of designs. Almost all of the walls have supporting ribs and many walls are corrugated. These patterns of construction will result in corresponding patterns of absorption of the x-rays. The uniformity of the patterns from an empty container can itself be the baseline for a self-correlation analysis of the data in which the repeat patterns of intensities in the scan of a single vehicle are intercompared to find significant changes in the pattern that signal the presence of a clandestine object.

On-line analysis of the vehicle by self-correlation methods that find anomalies in the patterns of counts are rapid and robust and do not require knowledge of the speed of the vehicle.

Another approach, which may be effective for a very wide class of vehicles, is to compare the images obtained during an inspection with images of the empty container, stored as a file in the computer memory. In many cases, the empty-container images may be accurately simulated by standard computer modeling techniques, using as input the manufactures specifications of the dimensions and composition of the container. For a vehicle that travels more or less regularly through the inspection point, the inspectors may obtain the fiducial image during a crossing when the container is certified as empty.

It should be noted that the described embodiments of the invention may be used in combination of two or more of the above embodiments in order to inspect the contents of the container. The described embodiments of the invention are intended to be merely exemplary and numerous variations and modifications will be apparent to those skilled in the art. All such variations and modifications are intended to be within the scope of the present invention as defined in the appended claims.

I claim:

1. An inspection system for inspecting an enclosure having a spatial frame of reference, comprising:
   (a) a source of penetrating radiation;
   (b) a collimator for forming the penetrating radiation into a beam having an orientation with respect to the enclosure;
   (c) a scanner arrangement for varying the orientation of the beam with respect to the enclosure such that a component of the beam traverses the enclosure;
   (d) a detector for producing flux position distribution information, disposed so as to intercept the component of beam traversing the enclosure;
   (e) a signal-processing means for transforming the position distribution information to an absorption distribution matrix referred to the spatial frame of reference of the enclosure; and
   (f) a controller for determining the presence of concealed material within the enclosure based at least on the absorption distribution matrix and a specified detection criterion.

2. The inspection system as set forth in claim 1 wherein the source of penetrating radiation is an x-ray source.

3. The inspection system as set forth in claim 1 wherein the source of penetrating radiation is an x-ray tube.

4. The inspection system as set forth in claim 1 wherein the beam is a beam of specified cross section.

5. The inspection system as set forth in claim 1, wherein the beam is a fan beam.

6. The inspection system as set forth in claim 1, wherein the scanner arrangement includes a conveyor for transporting the enclosure through the beam.

7. The inspection system as set forth in claim 1, wherein the detector includes a liquid scintillator.

8. The inspection system as set forth in claim 7, wherein the liquid scintillator includes heavy metal doping.

9. The inspection system as set forth in claim 7, wherein the liquid scintillator includes tin doping.

10. The inspection system as set forth in claim 1, further comprising a computer memory for storing absorption matrices of standard enclosures.

11. The inspection system as set forth in claim 1, wherein said detector includes an array of photodetectors.

12. The inspection system as set forth in claim 1, further comprising an autocorrelator for detecting repeat patterns and significant changes of absorption of penetrating radiation as the component of the beam traverses the enclosure.

13. The inspection system as set forth in claim 1, further comprising a visual display for displaying an image based on the absorption distribution matrix.

14. A method for detecting the presence of concealed material within an enclosure, comprising:
   (a) illuminating the enclosure with penetrating radiation propagating substantially along a beam having an orientation with respect to the enclosure;
   (b) varying the orientation of the beam with respect to the enclosure such that a component of the beam traverses the enclosure;
   (c) mapping an areal distribution of penetrating radiation transmitted through the enclosure;
   (d) processing the areal distribution of penetrating radiation transmitted through the enclosure to obtain an absorption distribution matrix; and
   (e) automatically determining the presence of concealed material within the enclosure.

15. The method for detecting the presence of concealed material within an enclosure according to claim 14, further comprising the step of comparing the absorption distribution matrix with stored absorption distribution matrices.

16. A method for detecting the presence of concealed material within an enclosure, comprising:
   (a) illuminating the enclosure with penetrating radiation propagating substantially along a beam having an orientation with respect to the enclosure;
   (b) varying the orientation of the beam with respect to the enclosure such that a component of the beam traverses the enclosure;
   (c) mapping an areal distribution of penetrating radiation transmitted through the enclosure;
   (d) autocorrelating the areal distribution of penetrating radiation transmitted through the enclosure; and
   (e) determining the presence of concealed material within the enclosure.

* * * * *